US00PP26412P2

(12) United States Plant Patent
Bedford et al.

(10) Patent No.: US PP26,412 P2
(45) Date of Patent: Feb. 16, 2016

(54) APPLE TREE NAMED 'MN55'

(50) Latin Name: *Malus domestica*
Varietal Denomination: MN55

(71) Applicants: David Bedford, New Germany, MN (US); James Luby, St. Paul, MN (US)

(72) Inventors: David Bedford, New Germany, MN (US); James Luby, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 111 days.

(21) Appl. No.: 13/999,373

(22) Filed: Feb. 18, 2014

Related U.S. Application Data

(60) Provisional application No. 61/851,791, filed on Mar. 13, 2013.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Penny J. Aguirre

(57) ABSTRACT

A new cultivar of apple tree, 'MN55', that is characterized by its fruit that is early ripening, its fruit that are globose-conical in shape and medium to large in size, its fruit with a texture that is very crisp and juicy, which is maintained during storage, its fruit with a long storage life, its fruit skin that is 75 to 95% red in color over a yellow-green background color, its firmness of 14 to 19 lbs. at harvest, its spreading to upright plant habit, and its vigorous growth habit.

1 Drawing Sheet

Botanical classification: *Malus domestica.*
Varietal denomination: 'MN55'.

BACKGROUND OF THE INVENTION

The present invention relates to a new and distinct cultivar of apple tree, botanically known as *Malus domestica* 'MN55', referred to hereafter by its cultivar name, 'MN55'.

'MN55' was selected as a single unique seedling tree by the Inventors as Tree 181 in Row 14 of Block 80C at a research center in Excelsior, Minn. The new apple tree arose from a cross designated as AE 97102 made in 1997 between 'Honeycrisp' (U.S. Plant Pat. No. 7,197) as the female parent and a selection made in an Arkansas apple breeding program designated as AA-44 (not patented, syn. 'Monark') as the male parent.

Asexual propagation of the new cultivar was first accomplished by budding in 1998 under the direction of the Inventors in Excelsior, Minn. Further asexual propagation by budding and grafting in Excelsior, Minn. has determined that the characteristic of the new cultivar are stable and are reproduced true to type in successive generations.

SUMMARY OF THE INVENTION

The following traits have been repeatedly observed and represent the characteristics of the new cultivar and distinguish 'MN55' as a unique cultivar of apple tree. The unique characteristics of 'MN55' were determined after 10 years of observation in Excelsior, Minn.

1. 'MN55' exhibits fruit that is early ripening; ripening about the third week in August in Excelsior, Minn.
2. 'MN55' exhibits fruit that is globose-conical in shape with a diameter of 7.1 to 7.6 cm (medium to large).

3. 'MN55' exhibits fruit with a texture that is very crisp and juicy, which is maintained during storage (especially unique for an early ripening cultivar).
4. 'MN55' exhibits fruit with a long storage life; 150 to 180 days (especially unique for an early ripening cultivar).
5. 'MN55' exhibits fruit skin that is 75 to 95% red in color over a yellow-green background color.
6. 'MN55' fruit has a firmness of 14 to 19 lbs. at harvest.
7. 'MN55' trees exhibit a spreading to upright plant habit.
8. 'MN55' trees exhibit a vigorous growth habit.

'MN55' differs from its female parent plant, 'Honeycrisp', in having fruit that ripens 3 to 4 weeks earlier. 'MN55' differs from its male parent, AA-44, in having a greater degree of red skin color and a much longer storage life. 'MN55' can be most closely compared to the cultivar, 'Minneiska' (U.S. Plant Pat. No. 18,812). 'MN55' is similar to 'Minneiska' in having crisp and juicy fruit that is maintained during storage. 'MN55' differs from 'Minneiska' in having fruit that is darker red in color, ripens 1 to 2 weeks earlier, and exhibits a longer storage life. 'MN55' also differs from 'Minneiska' in having a more vigorous growth habit.

BRIEF DESCRIPTION OF THE DRAWINGS

The accompanying color photograph was taken of fruit harvested from 'MN55' trees that were grown in a trial plot for approximately 10 years in Excelsior, Minn.

The photograph in FIG. 1 provides a view of three fruit of 'MN55'; a view of the calyx end on the left, a side view in the middle, and a view of the stem end on the right.

The colors in the photograph are as close as possible with the photographic and printing technology utilized and the color values cited in the detailed botanical description accurately describe the colors of the new apple tree.

DETAILED BOTANICAL DESCRIPTION

The following is a detailed description of the new apple variety as observed on trees grown for 10 years in Excelsior, Minn. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

Tree description:

*Habit*.—Upright to spreading.

*Growth rate*.—Vigorous.

*Diseases resistance*.—Has shown no observed resistance to apple scab on either the leaves or the fruit.

*Cold hardiness*.—U.S.D.A. Zone 4.

*Branching habit*.—Spreading.

*Branch frequency*.—Medium.

*Branch strength*.—Intermediate.

*Angle of bearing branches*.—Approximately 90°.

*Predominance of bearing*.—Both spurs and shoots.

Description of dormant shoots:

*Pubescence on upper one year-old shoot*.—Medium to heavy.

*Shine of bark*.—Weak to medium.

*Thickness of shoot at center of middle internode*.—Average of 5.09 mm.

*Bark color* (*using bark on* 1 *year old shoots exposed to sun*).—187B.

*Shoot angle*.—Approximately 90°.

*Lenticel*.—Medium to heavy in size and medium in number, color 159D.

Description of growing shoots:

*Color of growing tip of shoot*.—193C.

*Shape of shoot tips leaves in cross section*.—Concave.

*Pubescence of shoots tip leaves*.—Weak to medium on upper surface of leaf and dense on lower side.

*Color of shoot tip leaves*.—195C on lower surface and 196B on upper surface.

*Distribution of color other than green on shoot tips leaves*.—None.

Leaf description:

*Leaf orientation*.—Outward to upward.

*Leaf division*.—Simple.

*Leaf shape*.—Ovate.

*Leaf size*.—Average of 9.92 cm in length and 5.42 mm in width ($4^{th}$ to $6^{th}$ leaf).

*Leaf apex*.—Acuminate.

*Leaf base*.—Oblique or obtuse.

*Leaf surface*.—Moderately glossy on upper surface, pubescent on lower surface.

*Leaf margin*.—Mostly serrate.

*Leaf color*.—Upper surface 146A, lower surface 148B.

*Leaf anthocyanin on lower surface*.—None.

*Leaf venation*.—Pinnate main veins with netted minor veins.

*Petiole size*.—Average of 3.03 cm in length and 2 mm in diameter.

*Petiole color*.—144D.

*Stipules*.—Small to medium in size (mean 0.7 cm in length).

Flower description:

*Beginning flowering date*.—Ranging from April 23rd (early blooming years) to May 24th (late blooming years) and extending 4 to 8 days depending on weather conditions in Excelsior, Minn.

*Number of flowers*.—5 to 6, average of 5.36 per spur.

*Inflorescence type*.—Corymb of rotate flowers.

*Flower buds*.—At pink tip stage; 70D in color, round to conical in shape, average of 8.3 mm in length and 5.7 mm in diameter.

*Flower size*.—Average of 4.87 cm in diameter and 1.5 cm in depth.

*Flower fragrance*.—Mild.

*Flower aspect*.—Upright.

*Petals*.—5 to 6 per flower, un-fused, sometimes overlapping, ovate in shape, obtuse apex, entire margin, about 1.62 cm in width and 2.08 cm in length, color of upper and lower surface when opening; 155D, slightly tinged with 62C, color of upper and lower surface when fully open; 155D, slightly tinged with 62C and visible slightly more than the upper surface, upper and lower surface glabrous.

*Sepals*.—5 to 6, color upper and lower surface 142C, slight to moderately pubescent surface, triangular in shape, entire margin, acute apex, fused base, average of 6.4 mm in length and 3.7 mm in width.

*Pedicel*.—182A in color, average of 2.46 cm in length and 2 mm in width, glabrous surface.

*Pistil*.—1, with 5 styles, 90 mm in length, style is 149C in color and 70 mm in length, stigma is 149C in color, ovary is pubescent and 139D in color.

*Stamens*.—Average of 20, anther is oblong in shape, 8B in color and 2.1 mm in length, pollen is 5C in color and moderate in quantity.

*Pollination requirements*.—Self incompatible.

Fruit description:

*Fruit size*.—Medium to large, 7.1 to 7.6 cm in diameter, 6.3 to 6.9 cm in height.

*Position of maximum diameter*.—Slightly above the midway point between proximal and distal ends.

*Fruit shape*.—Globose-conical.

*Fruit symmetry*.—Mostly symmetrical.

*Fruit prominence of ribbing*.—Very weak.

*Fruit aperture of eye*.—Half open to closed.

*Size of eye*.—Medium, average of 9.2 mm.

*Persistence of calyx*.—Present.

*Length of sepal*.—Medium, average of 4.3 mm.

*Spacing of sepals at base*.—Touching to overlapping.

*Depth of eye basin*.—Medium, average of 5.8 mm.

*Width of eye basin*.—Medium, average of 19.4 mm.

*Thickness of stalk*.—Thin to medium, average of 2.0 mm.

*Length of stalk*.—Medium, average of 19.6 mm.

*Depth of stalk cavity*.—Medium, average of 8.4 mm.

*Width of stalk cavity*.—Medium, average of 20.5 mm.

*Relief of surface*.—Smooth with some hammered mottling.

*Bloom of skin*.—Light.

*Waxiness of skin*.—Absent.

*Thickness of skin*.—Medium.

*Skin color*.—75 to 95% 46A over a background color of 2B.

*Presence of russet*.—Very low level of presence, positioned around stalk cavity.

*Lenticels*.—Small (average of 0.5 mm), not prominent.

*Color of flesh*.—158C.

*Distinctness of core line*.—Medium.

*Aperture of locules*.—Moderately open.

*Fruit set*.—Intermediate to good.

*Fruit maturity date*.—Early, harvest is approximately the 3rd week in August, in east central Minnesota, 1 to 2 weeks prior to 'Minneiska' and 3 to 4 weeks prior to 'Honeycrisp'.

*Seed*.—199B in color when dry, ovoid to somewhat deltoid in shape, an average of 8.3 mm in length and 4.4 in diameter.

*Browning of flesh*.—Medium level.

*Firmness* (*without skin*).—Medium, 14 to 19 lbs at harvest.

*Texture of flesh*.—Very crisp and course; retained during storage.

*Cropping frequency*.—Some tendency to be biennial.

*Fruit flavor*.—Somewhat acidic when harvested early but well balanced at full maturity.

*Fruit weight*.—Average of 195.2 g (observed on 5 year-old trees grown on dwarfing rootstock in Excelsior, Minn.).

*Fruit productivity*.—33,015 lbs./acre (16.5 tons), 786.1 bushels/acre based on a 42 lb./bushel (observed on 5 year-old trees grown on dwarfing rootstock in Excelsior, Minn.).

*Juiciness*.—Juicy; retained during storage.

*Acidity*.—Average of 0.74 titratable acidity (malic acid equivalent).

*Brix*.—Average of 13.7°.

*Storage life*.—150 to 180 days in common stage (average temperature of 34° F.), unusually long storage life for an early ripening variety, longer than 'Minneiska'.

*Market use*.—Fresh Fruit (particularly suitable as a dessert apple.

It is claimed:

1. A new and distinct variety of apple tree named 'MN55' as herein illustrated and described.

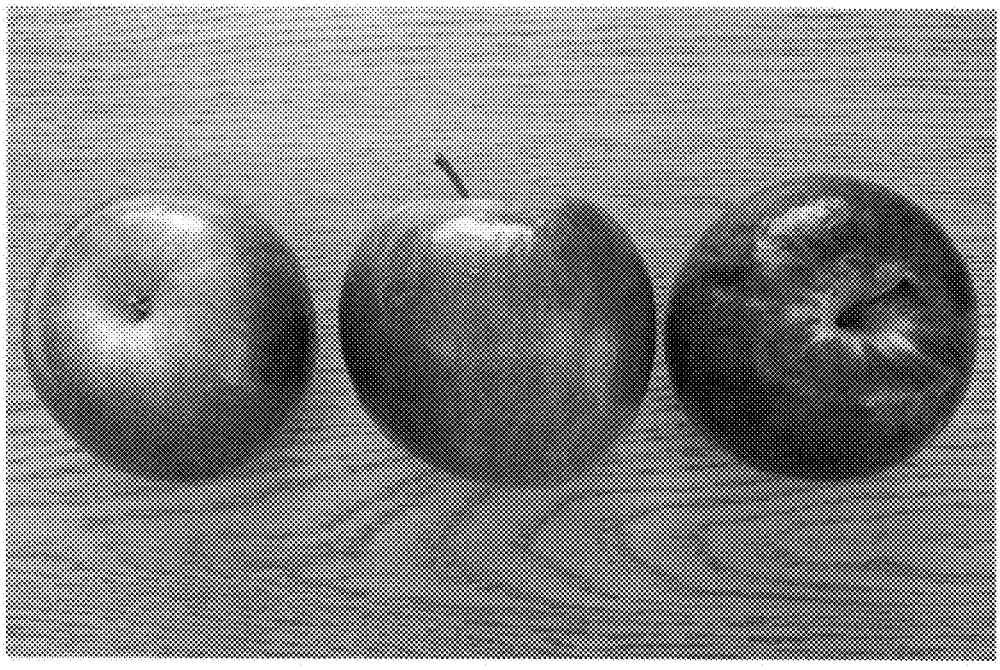

* * * * *